(12) United States Patent
Agbodoe et al.

(10) Patent No.: US 8,894,029 B2
(45) Date of Patent: Nov. 25, 2014

(54) RETRACTOR RING HOLDER

(75) Inventors: Victor Agbodoe, Raynham, MA (US); Olaf Storz, Emmingen (DE); John R. Bookwalter, Brattleboro, VT (US)

(73) Assignee: Specialty Surgical Instrumentation, Inc., Warsaw, IN (US)

( * ) Notice: Subject to any disclaimer, the term of this patent is extended or adjusted under 35 U.S.C. 154(b) by 300 days.

(21) Appl. No.: 13/249,452

(22) Filed: Sep. 30, 2011

(65) Prior Publication Data

US 2013/0082157 A1    Apr. 4, 2013

(51) Int. Cl.
    *A47F 5/00*    (2006.01)
(52) U.S. Cl.
    USPC ...... 248/309.1; 600/231; 600/233; 248/298.1
(58) Field of Classification Search
    USPC .......... 248/309.1, 99, 298.1; 602/17; 606/54, 606/56; 600/233, 210, 215, 231
    See application file for complete search history.

(56) References Cited

U.S. PATENT DOCUMENTS

| | | | |
|---|---|---|---|
| 199,507 A * | 1/1878 | Brubaker | 248/100 |
| 1,322,445 A * | 11/1919 | Hyer | 248/97 |
| 2,680,536 A * | 6/1954 | Kojan | 220/321 |
| 4,254,763 A | 3/1981 | McCready | |
| 4,424,724 A | 1/1984 | Bookwalter | |
| 4,805,599 A | 2/1989 | Ray | |
| 5,284,129 A | 2/1994 | Agbodoe | |
| 5,375,481 A | 12/1994 | Cabrera | |
| 5,656,012 A * | 8/1997 | Sienkiewicz | 600/204 |
| 5,674,186 A * | 10/1997 | Guigui et al. | 602/17 |
| 5,951,467 A | 9/1999 | Picha | |
| 6,190,312 B1 | 2/2001 | Fowler, Jr. | |
| 6,302,843 B1 | 10/2001 | Lees | |
| 6,468,207 B1 | 10/2002 | Fowler, Jr. | |
| 6,659,945 B2 | 12/2003 | Ball | |
| 6,808,493 B1 | 10/2004 | Bookwalter | |
| 7,166,113 B2 | 1/2007 | Arambula | |
| 2005/0119531 A1 | 6/2005 | Sharratt | |
| 2007/0101529 A1* | 5/2007 | Garcia | 15/169 |
| 2008/0302924 A1* | 12/2008 | Albert | 248/99 |

\* cited by examiner

*Primary Examiner* — Amy J Sterling
(74) *Attorney, Agent, or Firm* — Hayes Soloway P.C.

(57) ABSTRACT

A retractor ring assembly includes a ring holder that has a first selectively engaged connection and a second selectively engaged connection. A first and second ring portion each has a proximal end and a distal end. The proximal end of the first and second ring portions are selectively connected to the respective first and second selectively engaged connections of the ring holder. The distal end of the first ring portion has a third selectively engaged connection. The distal end of the second ring portion has a fourth selectively engaged connection. The third selectively engaged connection and the fourth selectively engaged connection are connectable to form a reinforced closed ring configuration, and are disconnectable to form an open ring configuration.

20 Claims, 9 Drawing Sheets

RETRACTOR RING HOLDER

FIELD OF THE INVENTION

The present invention relates to methods and devices for an adjustable retractor ring system having interchangeable rings.

BACKGROUND OF THE INVENTION

Figure 1:
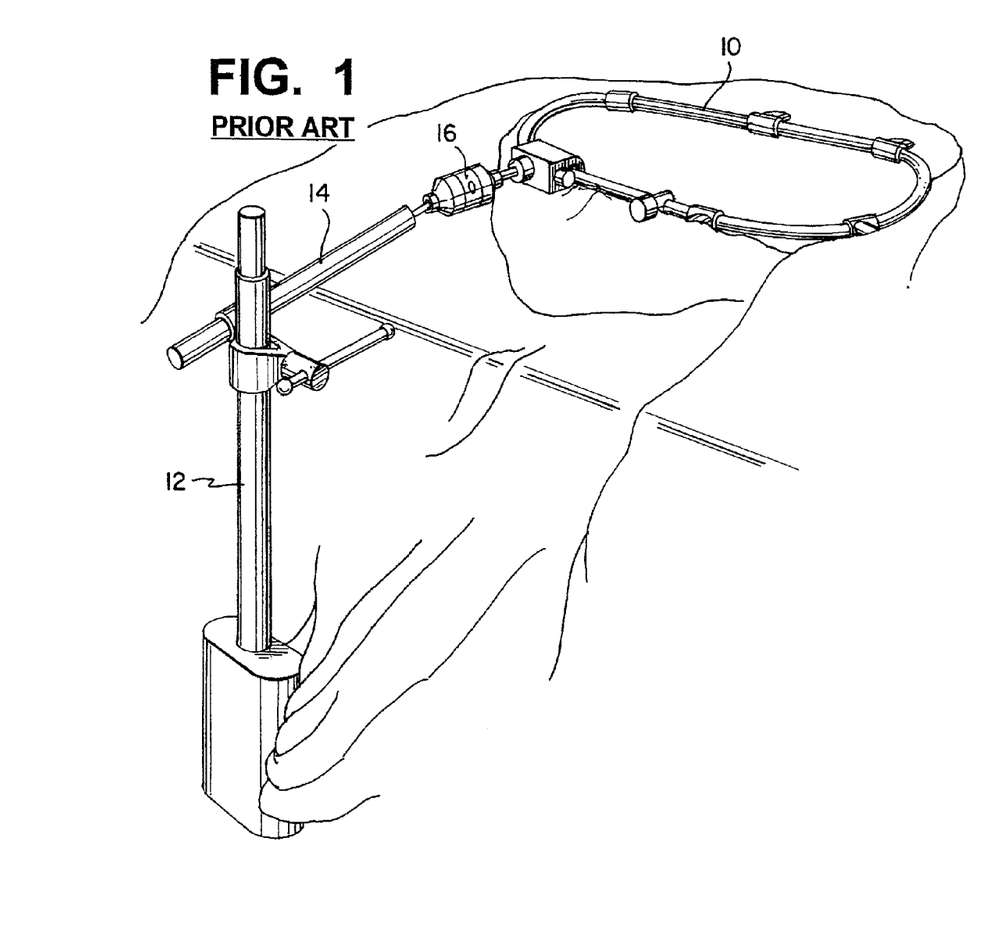
FIG. 1 is a plan view of a conventional ring holder.

During surgery, retractors, such as those found in the BOOKWALTER™ retractor kit, which is commercially available from Codman & Shurtleff, Inc. of Raynham, Mass., are often used to assist the surgeon and other operating room personnel to provide exposure to the surgical site for a broad range of surgical procedures. In surgical operations of the chest or abdomen, for example, it is often necessary to use a retraction apparatus to retain tissue away from the operative site. Typically, the refraction apparatus includes a housing member configured to lock onto a circumferential ring 10 located above the operative site (see FIG. 1). To maintain ring 10 in a fixed position, ring 10 can be connected to a support post 12 adjacent to the site by a horizontal bar 14 that has a flexible joint 16 (horizontal flex bar) to permit ring 10 to be oriented in various positions, as shown in FIG. 1. A horizontal extension arm may also be attached to the support post for supporting the circumferential ring. Within the housing member a refraction blade can usually be found for grabbing the tissue around the surgical incision. The housing member can also include a ratcheting mechanism and/or a tilting mechanism to draw the retraction blade away from the incision, thereby effecting the pulling away and/or lifting of the tissue around the incision to expose the desired surgical area. Examples of such retractor systems are disclosed in U.S. Pat. Nos. 4,254,763, 4,424,724, 5,375,481 and 6,808,493, the disclosures of which are hereby incorporated by reference in their entirety. During open surgical operations, such as, for example, open bariatric, ALIF procedures, hepatic resections, transplant procedures, abdominal aortic aneurysms, hernia repair, appendectomy and others, many different instruments are used, such as, for example, a retractor blade with ring attachment systems are used. In some medical procedures, different size rings are required to accommodate different procedures, different size patients, different doctor preference, etc. In addition, in some medical procedures, the doctor may want to separate the ring so that one half ring is in one plane and the other half ring is spaced from and in a different plane from the other half ring.

Thus, despite these refraction systems, there continues to be a need for a retraction system that can securely hold a retractor ring while permitting the size of the ring to vary.

SUMMARY OF THE INVENTION

The present invention includes a retractor ring assembly includes a ring holder that has a first selectively engaged connection and a second selectively engaged connection. A first and second ring portion each has a proximal end and a distal end. The proximal end of the first and second ring portions are selectively connected to the respective first and second selectively engaged connections of the ring holder. The distal end of the first ring portion has a third selectively engaged connection. The distal end of the second ring portion has a fourth selectively engaged connection. The third selectively engaged connection and the fourth selectively engaged connection are connectable to form a reinforced closed ring configuration, and are disconnectable to form an open ring configuration.

The present invention also includes a retractor ring kit. The kit includes a ring holder having a first selectively engaged connection and a second selectively engaged connection. A first ring portion has a proximal end and a distal end. The proximal end is selectively connected to the first selectively engaged connection of the ring holder. A second ring portion has a proximal end and a distal end. The proximal end is selectively connected to the second selectively engaged connection of the ring holder. The first and second ring portions have approximately the same shape. A third ring portion has a proximal end and a distal end. The proximal end is selectively connected to the first selectively engaged connection of the ring holder. A fourth ring portion has a proximal end and a distal end. The proximal end is selectively connected to the second selectively engaged connection of the ring holder. The third and fourth ring portions have approximately the same shape and that shape is different from the shape of the first and second ring portions.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides methods and devices for an adjustable retractor ring system having interchangeable rings. A retractor ring holder 20 is illustrated in FIGS. 2, 3, 7 and 11. Ring holder 20 includes a post connecting portion 22 and a ring holder portion 24. Post connecting portion 22 has a proximal end 26 and a distal end 28. Proximal end 26 connects to a table post 12 or to a horizontal extension bar (not shown) in a manner known to those skilled in the art. Distal end 28 of post connecting portion 22 is fixedly connected to ring holder 24 by an annual mating serrated saw-like connection 30, which may also be referred to as a starburst connection. Connection 30 is selectively loosened and tightened by moving collar 32 either toward or away from the distal end 28 of post connecting portion 22. In the loosened position, ring holder portion 24 is free to rotate 360 degrees with respect to bar portion 22. In the tightened position, however, ring holder portion 24 is fixedly connected to bar portion 22.

Figure 2A:
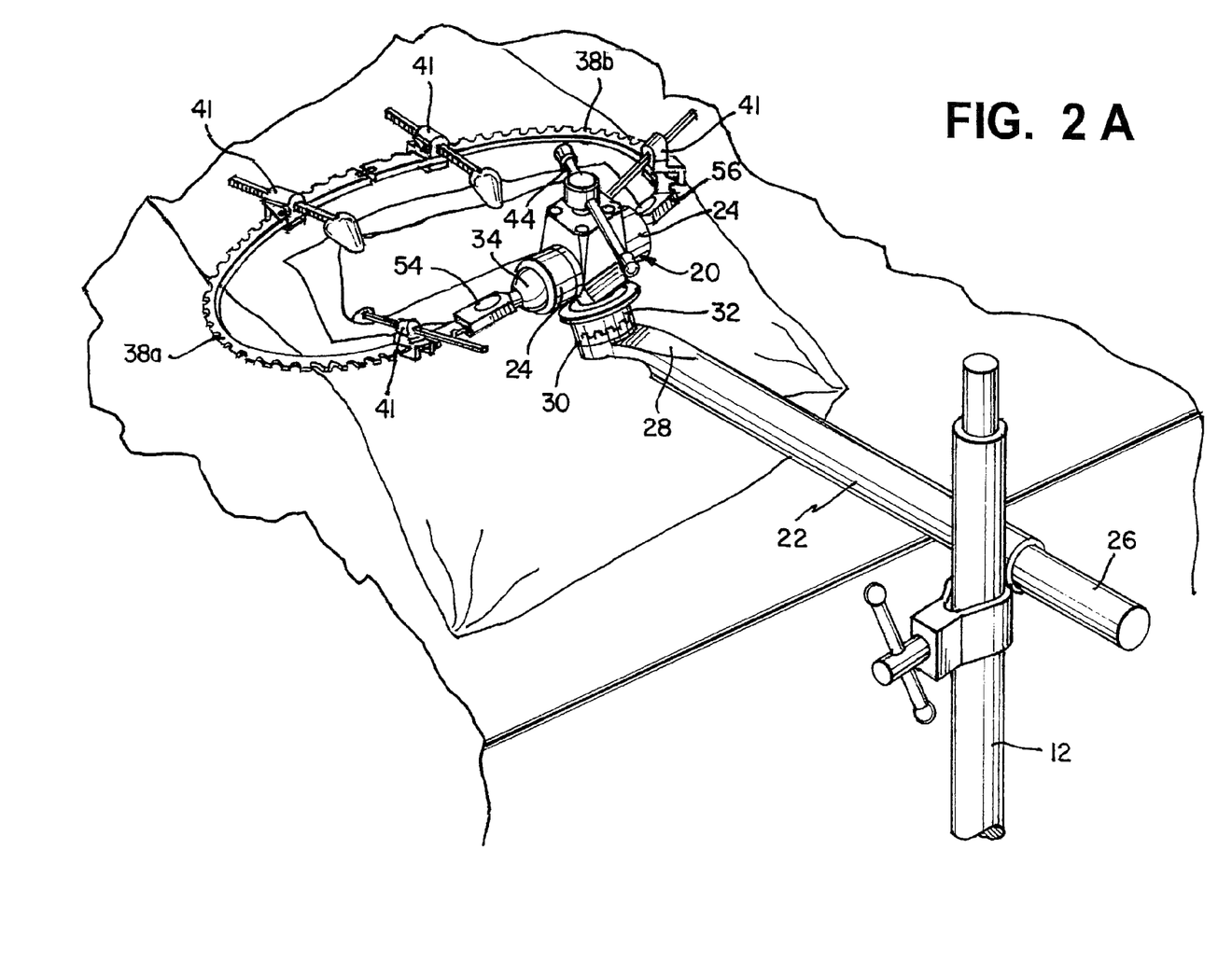
FIG. 2A is a plan view of the ring holder and a pair of ring portions in accordance with the present invention.
Figure 2B:
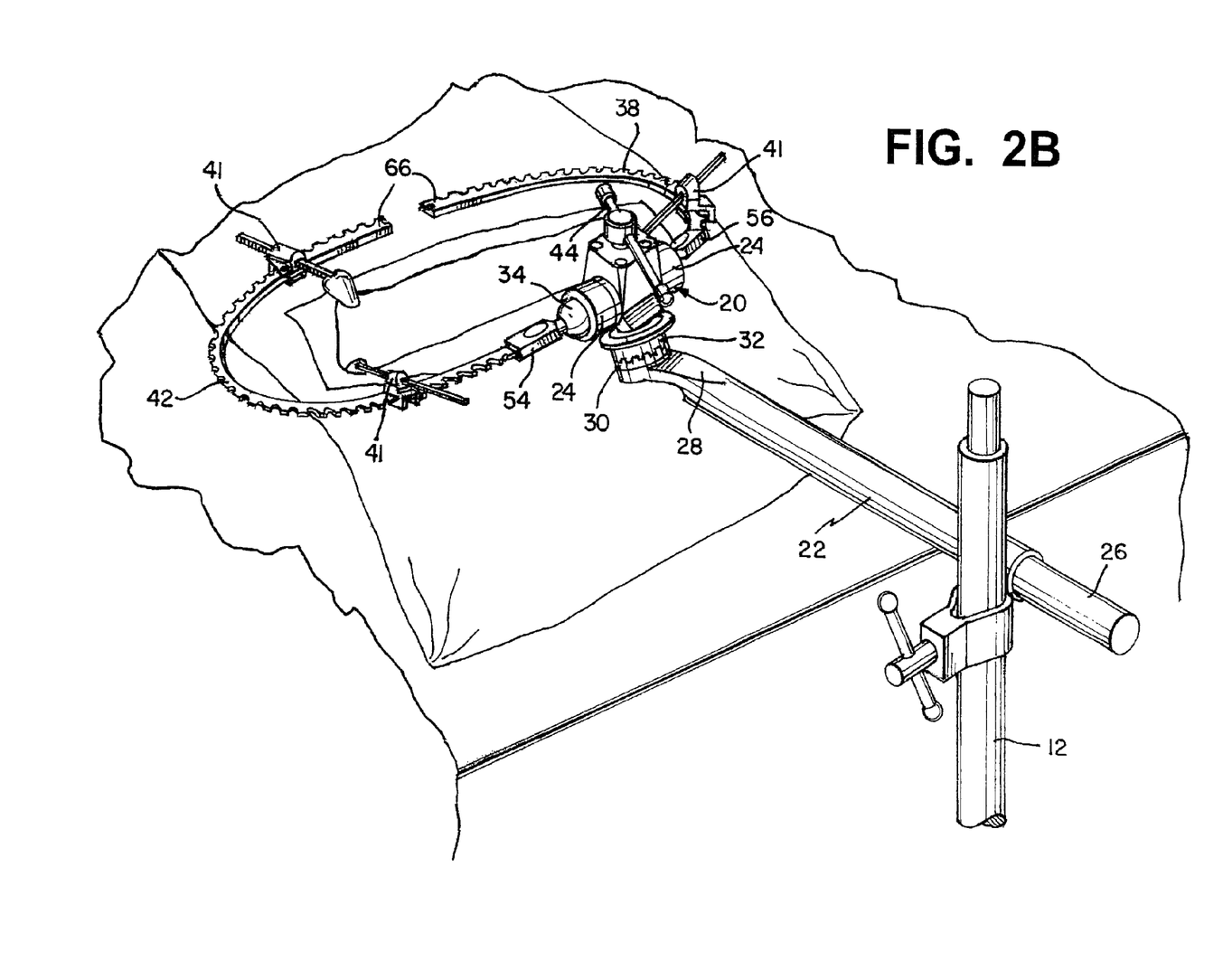
FIG. 2B is a plan view of the ring holder and a pair of ring portions in accordance with the present invention.
Figure 3:
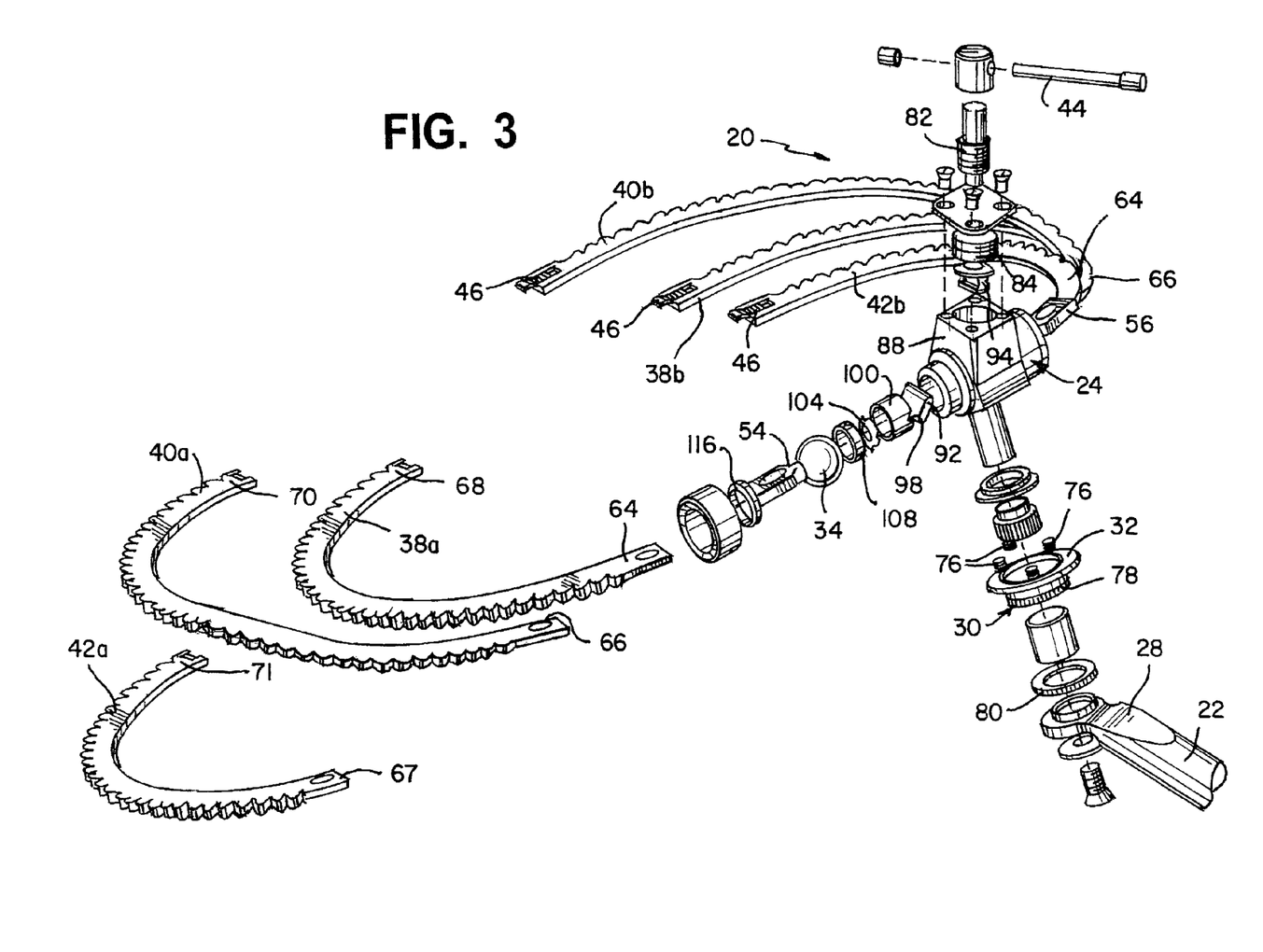
FIG. 3 is an exploded view of the ring holder and the sets of ring pairs.
Figure 4A:
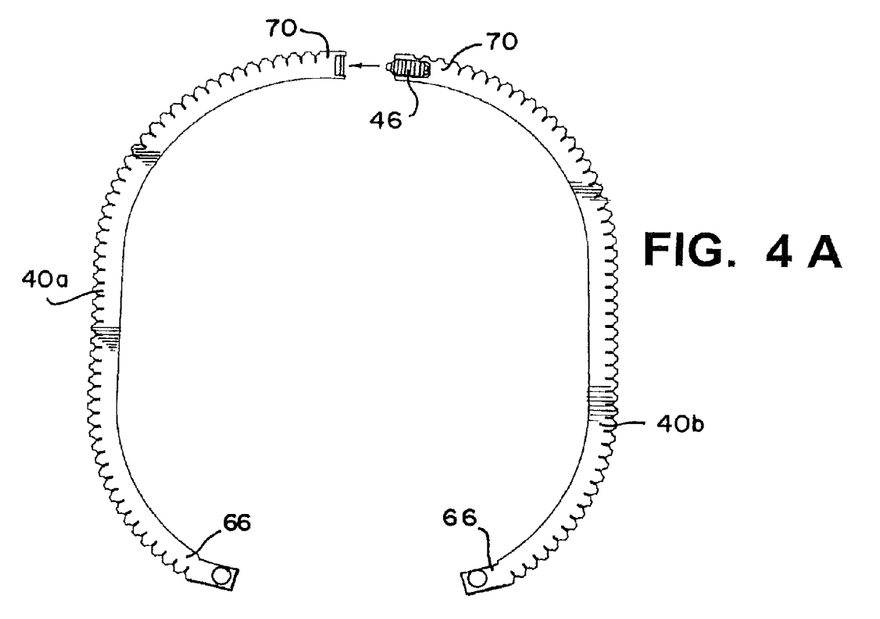
FIG. 4A is a top view of the first set of ring pairs.
Figure 4B:
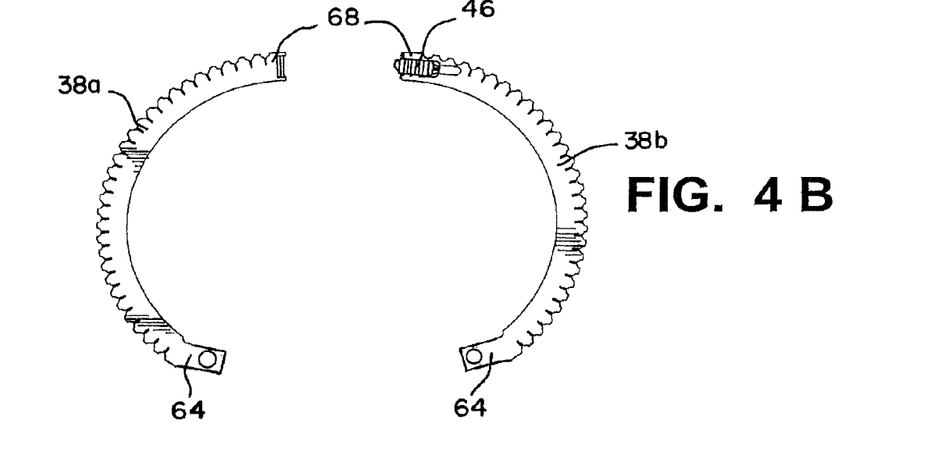
FIG. 4B is a top view of the second set of ring pairs.
Figure 4C:
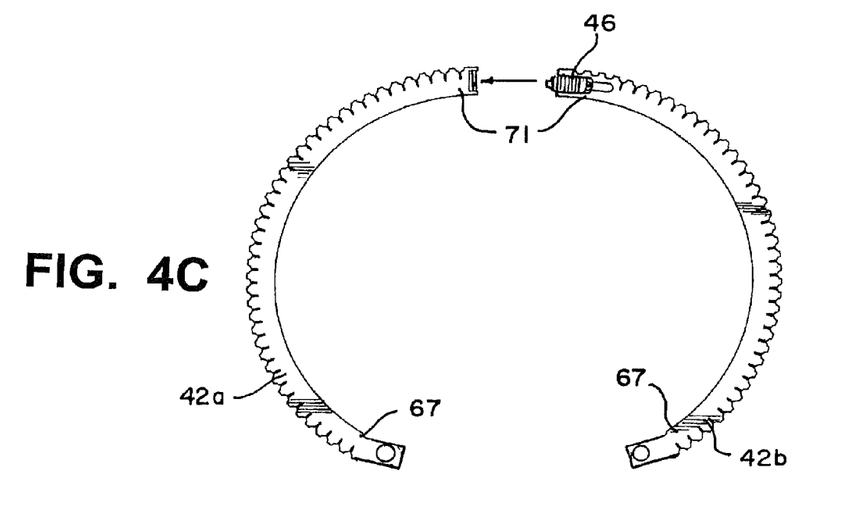
FIG. 4C is a top view of the third set of ring pairs.

Ring holder portion 24 includes a first ball joint connection 34 and a second ball joint connection 36. Referring now to FIGS. 2-7, the quick connection/disconnection of a plurality of sets of ring portions 38a, 38b; 40a, 40b; and 42a, 42b are illustrated. Rotation of a handle 44 in either a clockwise or counter-clockwise direction, will selectively lock the position of portions 38a, 38b; 40a, 40b; and 42a, 42b in place or unlock the ring portions so that they can be selectively positioned in any desired location by the user and thereafter locked in place by rotation of handle 44. If should be noted that the ring pairs 38a, 38b; 40a, 40b; and 42a, 42b may be utilized so that rings of the same size are used together as shown in FIG. 2A with ring pair 38a, 38b, or ring pairs of different sizes may be used as shown in FIG. 2B with ring pair 38a, 42b, for example. A plurality of retractor blades 41 may be affixed to the rings 38a, 38b, 40a, 40b, 42a and 42b, as shown in FIGS. 2A and 2B.

Figure 5:
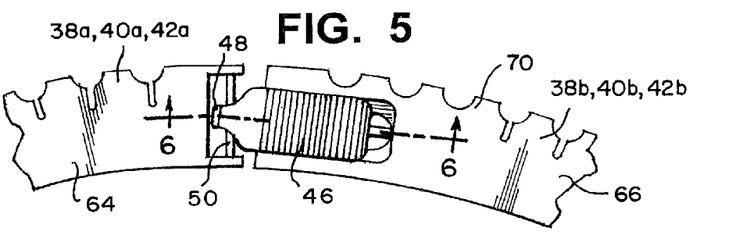
FIG. 5 is an enlarged top view of one of the distal end of one of the sets of ring pairs.

Referring now to FIGS. 4-7, each ring portion pair 38a, 38b; 40a, 40b; and 42a, 42b are movable between a selectively engaged position and a selectively disengaged position. When in the selectively engaged position, as shown in FIGS. 5 and 6a, the ring pairs form a reinforced closed ring. When in the selectively engaged position, as shown in FIGS. 2, 4a, 4b, 4c and 6b, the ring pairs are disconnected to form an open ring position. To assist in connecting and disconnecting the ring pairs, a sliding latch is provided on distal end of each ring portion 38b, 40b and 42b. Latch 46 has a distal free end 48. The distal end of each ring portion 38a, 40a, 42a has a locking pin 50 rigidly fixed in place. To disconnect the ring pair from the selectively engaged position, the user will push latch 46 in the direction indicated by arrow A in FIG. 6B thereby moving the distal end 48 of latch 46 to the open position as shown in FIG. 6B. The user can then angle the respective ring portion 38a, 40a, 42a upwardly in the direction indicated by arrow B to the position illustrated in FIG. 6B, and remove the respective ring portion 38a, 40a, 42a from being selectively engaged from ring portion 38b, 40b and 42b.

Figure 6A:
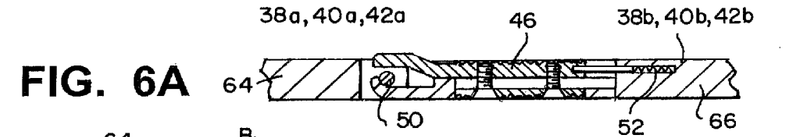
FIG. 6A is cross-sectional view taken along line 6-6 of FIG. 5 and looking in the direction of the arrows.
Figure 6B:
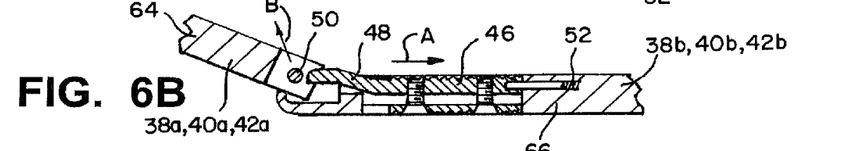
FIG. 6B is cross-sectional view taken along line 6-6 of FIG. 5 and looking in the direction of the arrows.
Figure 7:
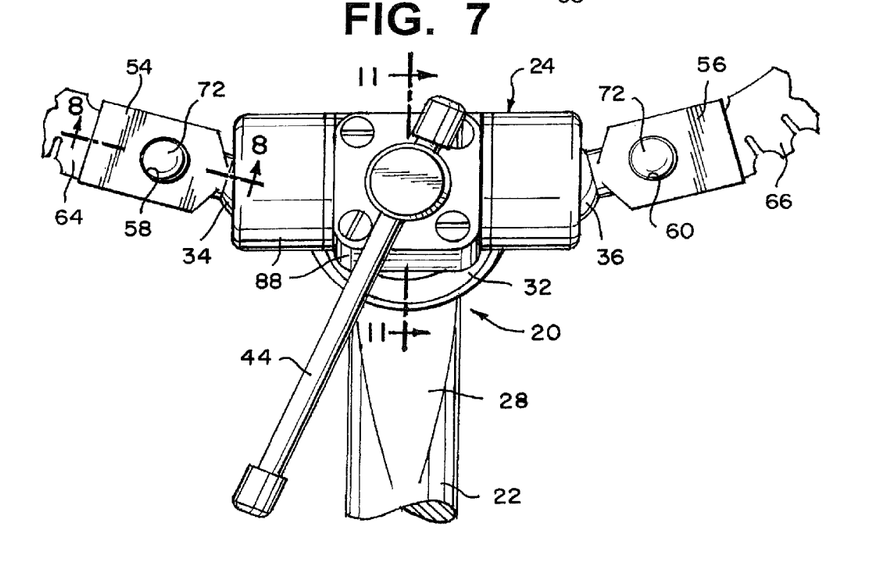
FIG. 7 is a top view of the ring holder.

The user will utilize the opposite steps to connect the ring pairs. For example, the user will push latch 46 in the direction indicated by arrow A in FIG. 6B thereby moving the distal end 48 of latch 46 to the open position as shown in FIG. 6B. The user can then angle the respective ring portion 38a, 40a, 42a downwardly in the opposite direction than that indicated by arrow B in FIG. 6B. Latch 46 can be released. Latch 46 is spring biased by spring 52 into the position shown in FIG. 6A. As shown in FIG. 6A, the respective ring portion 38a, 40a, 42a is selectively engaged with the respective ring portion 38b, 40b and 42b.

Figure 8A:
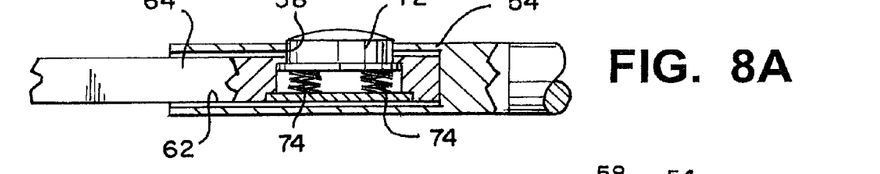
FIG. 8A is cross-sectional view taken along line 8-8 of FIG. 7 and looking in the direction of the arrows.
Figure 8B:
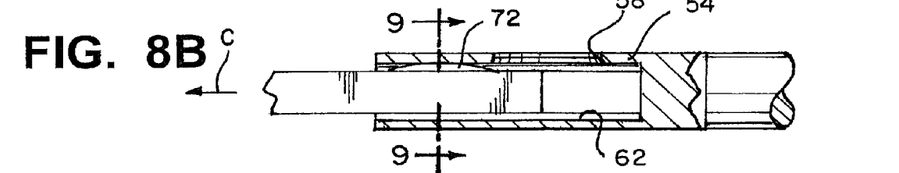
FIG. 8B is cross-sectional view taken along line 8-8 of FIG. 7 and looking in the direction of the arrows.
Figures 9, 10, 11, 12:
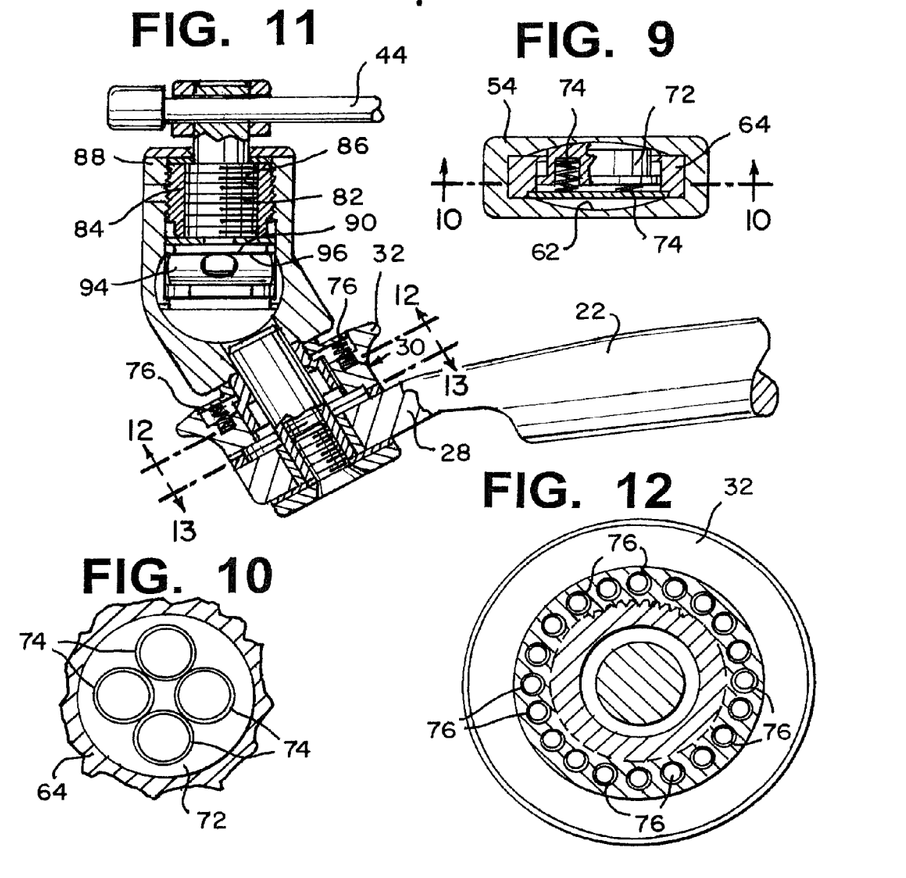
FIG. 9 is cross-sectional view taken along line 9-9 of FIG. 8B and looking in the direction of the arrows.
FIG. 10 is cross-sectional view taken along line 10-10 of FIG. 9 and looking in the direction of the arrows.
FIG. 11 is a side view, with parts broken away, of the ring holder.
FIG. 12 is cross-sectional view taken along line 12-12 of FIG. 11 and looking in the direction of the arrows.
Figure 13:
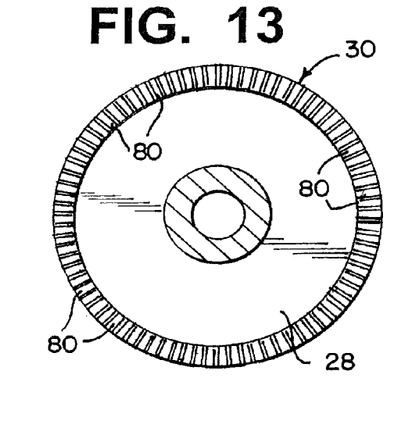
FIG. 13 is cross-sectional view taken along line 13-13 of FIG. 11 and looking in the direction of the arrows.

Referring now to FIGS. 7-10, the mechanism for selectively connecting a ring portion 38a, 38b, 40a, 40b, 42a and 42b to the ring holder portion 24 of ring holder 20 is shown. Ring holder portion 24 has a first sleeve 54 and a second sleeve 56. Each sleeve 54, 56 has a respective opening 58, 60 on its top surface. Each sleeve has an internal blind bore or channel 62 (the blind bore for sleeve 56 is not shown, but it has the same shape as bore 62). Each ring portion 38a, 38b, 40a, 40b, 42a and 42b has a proximal end 64, 66 and a distal end 68, 70. Proximal end 64, 66 is selectively connected to the ring holder portion 24 of ring holder 20. The proximal end of each ring portion has a spring biased button 72. Preferably, as shown in FIG. 10, four springs 74 are utilized to bias button 72 into the connected position of FIG. 8. To disconnect a ring portion from the ring holder 20, the user will push down on button 72 and substantially simultaneously pull on the ring portion in the direction indicated by arrow C in FIG. 8B to remove the ring portion proximal end 64 from sleeve 54, 56.

The user will utilize the opposite steps to connect the ring portion to the ring holder 20. For example, the user will push the desired ring portion 38a, 38b, 40a, 40b, 42a and 42b in the direction opposite to that indicated by arrow C in FIG. 8B thereby moving the proximal end 64 of the ring portion into channel 62. As the proximal end 64 enters channel 62, pin 72 will be biased into the ring portion as shown in FIGS. 8B and 9. The user will continue to push the proximal end of the ring portion into sleeve 62 until button 72 snaps up into opening 58, 60, thereby connecting or locking the ring portion into engagement with the ring holder 20.

Figure 14:
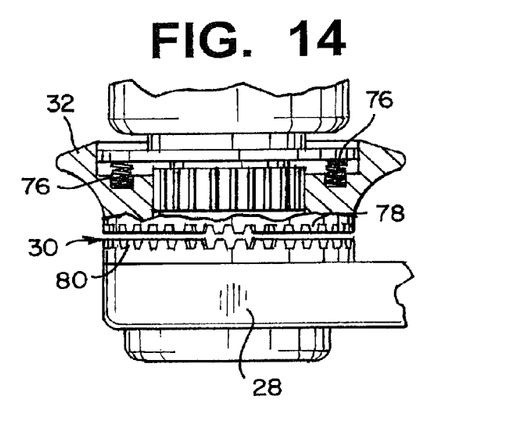
FIG. 14 is an enlarged side view, with parts broken away, of the starburst connection.
Figure 15A:
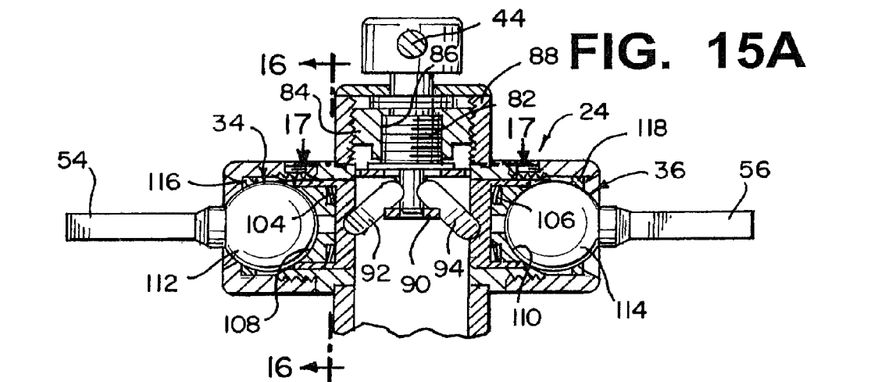
FIG. 15A is an enlarged side view, with parts broken away, of the ring holder.
Figure 15B:
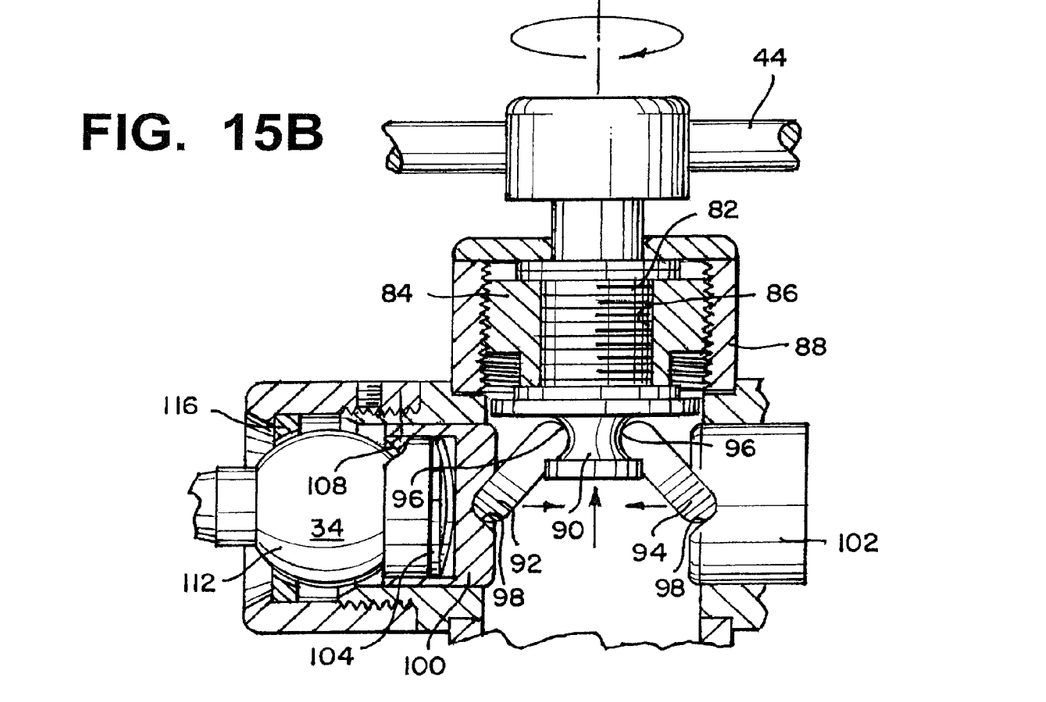
FIG. 15B is an enlarged side view, with parts broken away, of the ring holder.
Figure 16:
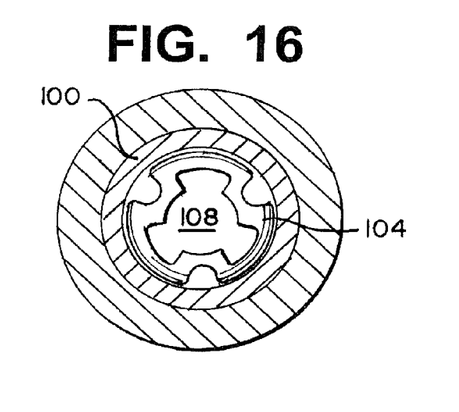
FIG. 16 is cross-sectional view taken along line 16-16 of FIG. 15A and looking in the direction of the arrows.
Figure 17:
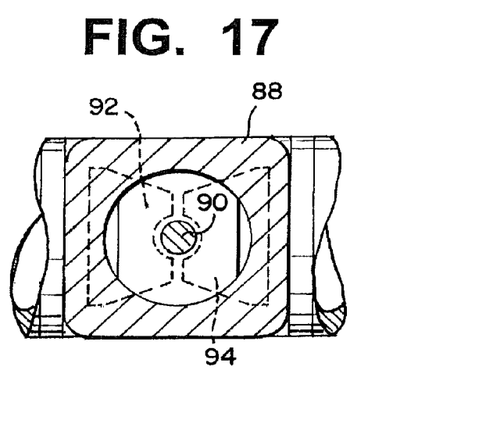
FIG. 17 is cross-sectional view taken along line 17-17 of FIG. 15A and looking in the direction of the arrows.

Referring now to FIGS. 11-14, once a desired ring portion pair 38a, 38b; 40a, 40b; and 42a, 42b are connected to the ring holder 20, the user can then adjust the position of the ring portion pair by rotating the ring holder 20 360° by use of collar 32 and starburst connection 30. As discussed above, connection 30 is selectively loosened and tightened by moving collar 32 either toward or away from the distal end 28 of post connecting portion 22. In the loosened position, as shown in FIG. 14, ring holder portion 24 is free to rotate 360 degrees with respect to bar portion 22. In the tightened position, however, ring holder portion 24 is fixedly connected to bar portion 22. Collar 32 is spring biased into the tightened position by a plurality of springs 76. Connection 30 is formed by a pair of mating annular serrated teeth 78, 80.

Referring now to FIGS. 11 and 15-17, the ring portion pair 38a, 38b; 40a, 40b; and 42a, 42b that is connected to the ring holder 20, can be further adjusted by the user by rotating handle 44 to adjust the position of the ring portion pair by moving the first ball joint connection 34 and the second ball joint connection 36 into the position desired by the user. Referring now to FIGS. 15A and 15B, rotation of rod 44 causes threaded rod 82 to rotate within a bushing 84 that has a mating threaded inner surface 86. Bushing 84 is fixedly connected to the housing wall 88 of the ring holder 20. The lower portion of rod 82 has a toggle lever bearing 92 protruding downwardly therefrom. A pair of toggle levers 92, 94 each have one end received in a recessed surface 96 of the toggle lever bearing 92. The other end of toggle levers 92, 94 are received in a notch 98 in a disc spring bushing 100, 102. A disc spring 104, 106 is disposed on the opposite side of the disc spring bushing 100, 102. A socket 108, 110 is disposed between the ball 112, 114 and the disc spring 104, 106. A ball washer 116, 118 is disposed between the opposite side of ball 112, 114 and the housing wall 88. FIG. 15A shows the ball joint connection in the locked position, and FIG. 15B shows the ball joint connection in the unlocked position, as evidenced by the space between ball 112 and ball washer 116, and socket 108. In the unlocked position the user may adjust the position of each ring portion, and then rotate handle 44 to lock the ring portions in the desired position. In the unlocked position ball 112 is prevented from being removed from housing 88 by ball washer 116, and socket 108. Thus, there is a preset load on handle 44 that prevents the ball and sleeve mechanism from being removed from the housing and permitting the ball and sleeve mechanism to be quickly locked in place by rotation of handle 44.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A retractor ring assembly comprising:
    a ring holder having a first selectively engaged connection and a second selectively engaged connection, wherein each of the first selectively engaged connection and the second selectively engaged connection are connected to the ring holder with a ball joint connection;
    a first ring portion having a proximal end and a distal end, the proximal end being selectively connected to the first selectively engaged connection of the ring holder, the distal end having a third selectively engaged connection; and
    a second ring portion having a proximal end and a distal end, the proximal end being selectively connected to the second selectively engaged connection of the ring holder, the distal end having a fourth selectively engaged connection, wherein the third selectively engaged connection and the fourth selectively engaged connection are connectable to form a reinforced closed ring configuration, and are disconnectable to form an open ring configuration, wherein the first selectively engaged connection has a sleeve including a channel therein, and the second selectively engaged connection has a sleeve including a channel therein, wherein the sleeve of each of the first selectively engaged connection and the second selectively engaged connection has an opening through a wall thereof.

2. The retractor ring assembly according to claim 1, further comprising a sliding latch slidably connected to the distal end of the second ring portion, wherein the latch has a free end.

3. The retractor ring assembly according to claim 1, wherein the distal end of the first ring portion has a pin fixedly connected thereto.

4. The retractor ring assembly according to claim 2, wherein the latch is spring-biased into a closed position with at least one spring, wherein the at least one spring is engaged between a restricted end of the latch and the second ring portion, wherein the restricted end is substantially opposite the free end.

5. A retractor ring kit comprising:
    a ring holder having a first selectively engaged connection and a second selectively engaged connection;
    a first ring portion having a proximal end and a distal end, the proximal end being selectively connected to the first selectively engaged connection of the ring holder;
    a second ring portion having a proximal end and a distal end, the proximal end being selectively connected to the second selectively engaged connection of the ring holder, wherein the first and second ring portions have approximately the same shape;
    a third ring portion having a proximal end and a distal end, the proximal end being selectively connected to the first selectively engaged connection of the ring holder; and
    a fourth ring portion having a proximal end and a distal end, the proximal end being selectively connected to the second selectively engaged connection of the ring holder, wherein the third and fourth ring portions have approximately the same shape that is different from the shape of the first and second ring portions; and
    at least two sliding latches, wherein a first of the at least two sliding latches is slidably connected to the distal end of the second ring portion and a second of the at least two sliding latches is slidably connected to the distal end of the fourth ring portion, wherein the first sliding latch is positioned at least partially within a cavity formed within the distal end of the second ring portion and the second sliding latch is positioned at least partially within a cavity formed within the distal end of the fourth ring portion.

6. The retractor ring kit according to claim 5, further comprising:
    a fifth ring portion having a proximal end and a distal end, the proximal end being selectively connected to the first selectively engaged connection of the ring holder; and
    a sixth ring portion having a proximal end and a distal end, the proximal end being selectively connected to the second selectively engaged connection of the ring holder, wherein the fifth and sixth ring portions have approximately the same shape that is different from the shape of the first and second ring portions and that is different from the shape of the third and fourth ring portions.

7. The retractor ring kit according to claim 5, wherein the first selectively engaged connection has a sleeve including a channel therein, and the second selectively engaged connection has a sleeve including a channel therein.

8. The retractor ring kit according to claim 7, wherein the sleeve of each of the first selectively engaged connection and the second selectively engaged connection has an opening through a wall thereof.

9. The retractor ring kit according to claim 8, wherein each ring portion has a spring biased button disposed at its proximal end.

10. The retractor ring kit according to claim 8, wherein, in the selectively engaged position between the ring portion and the ring holder, the proximal end of the ring portion is disposed within the sleeve and the spring biased button is disposed in the opening.

11. The retractor ring kit according to claim 8, wherein the sleeve of each of the first selectively engaged connection and the second selectively engaged connection further comprises an internal blind bore.

12. The retractor ring kit according to claim 11, wherein each internal blind bore further comprises a shaped surface, wherein the shaped surface substantially matches a shape of a top of a spring-biased button disposed on the proximal end of each ring portion.

13. The retractor ring assembly of claim 2, wherein the free end of the latch is slidable between a first position substantially aligned with a terminating face of the distal end of the second ring portion and a second positioned withdrawn from alignment with the terminating face of the distal end of the second ring portion.

14. The retractor ring assembly of claim 2, wherein a top surface of the sliding latch is substantially aligned with a top surface of the second ring portion.

15. The retractor ring assembly of claim 1, wherein each ring portion has a spring biased button disposed at its proximal end.

16. The retractor ring assembly of claim 1, wherein, in the selectively engaged position between the ring portion and the ring holder, the proximal end of the ring portion is disposed within the sleeve and the spring biased button is disposed in the opening.

17. The retractor ring assembly of claim 1, wherein the sleeve of each of the first selectively engaged connection and the second selectively engaged connection further comprises an internal blind bore.

18. The retractor ring assembly of claim 17, wherein for each of the first and second ring portions, a terminating end of the proximal end contacts an end face of the internal blind bore.

19. The retractor ring assembly of claim 17, wherein the internal blind bore is substantially rectangular.

20. The retractor ring assembly of claim 15, wherein the spring biased button further comprises a button biased by four springs, wherein the four springs are positioned within the proximal end of each of the ring portions.

* * * * *

UNITED STATES PATENT AND TRADEMARK OFFICE
CERTIFICATE OF CORRECTION

PATENT NO. : 8,894,029 B2  
APPLICATION NO. : 13/249452  
DATED : November 25, 2014  
INVENTOR(S) : Victor Agbodoe, Olaf Storz and John R. Bookwalter Page 1 of 1

It is certified that error appears in the above-identified patent and that said Letters Patent is hereby corrected as shown below:

In the Specification

Col. 1, Line 19, "refraction" should be --retraction--.

Col. 1, Line 29, "refraction" should be --retraction--.

Col. 1, Line 51, "refraction" should be --retraction--.

Signed and Sealed this  
Third Day of March, 2015

Michelle K. Lee  
*Deputy Director of the United States Patent and Trademark Office*